US010780295B2

(12) United States Patent
DeLuca et al.

(10) Patent No.: US 10,780,295 B2
(45) Date of Patent: Sep. 22, 2020

(54) METHOD FOR TREATING MULTIPLE SCLEROSIS

(71) Applicant: Wisconsin Alumni Research Foundation, Madison, WI (US)

(72) Inventors: Hector F. DeLuca, Deerfield, WI (US); Yanping Wang, Madison, WI (US); Steven Marling, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 13/773,254

(22) Filed: Feb. 21, 2013

(65) Prior Publication Data

US 2013/0253621 A1 Sep. 26, 2013

Related U.S. Application Data

(63) Continuation-in-part of application No. 13/576,253, filed as application No. PCT/US2011/023608 on Feb. 3, 2011, now abandoned.

(60) Provisional application No. 61/663,401, filed on Jun. 22, 2012, provisional application No. 61/301,820, filed on Feb. 5, 2010.

(51) Int. Cl.
*A61N 5/06* (2006.01)

(52) U.S. Cl.
CPC .... *A61N 5/0622* (2013.01); *A61N 2005/0637* (2013.01); *A61N 2005/0661* (2013.01)

(58) Field of Classification Search
CPC .. A61N 5/0613; A61N 5/0616; A61N 5/0618; A61N 2005/064; A61N 2005/0661

USPC .................................................... 607/88–94
See application file for complete search history.

(56) References Cited

U.S. PATENT DOCUMENTS

| 7,985,219 | B2 | 7/2011 | Wilkens et al. |
| 8,287,524 | B2 | 10/2012 | Sigel |
| 2003/0045916 | A1 | 5/2003 | Anderson et al. |
| 2005/0085878 | A1 | 4/2005 | Wilkens et al. |
| 2006/0013454 | A1 | 1/2006 | Flewelling et al. |
| 2006/0292182 | A1 | 12/2006 | Kemeny et al. |
| 2007/0106284 | A1* | 5/2007 | Siegel .......................... 606/15 |
| 2007/0185553 | A1 | 8/2007 | Kennedy |

(Continued)

FOREIGN PATENT DOCUMENTS

| CA | 2435916 | 9/2002 |
| WO | 2008061197 A2 | 5/2008 |

(Continued)

OTHER PUBLICATIONS

Hauser et al., "Prevention of experimental allergic encephalomyelitis (EAE) in the SJL/J mouse by whole body ultraviolet irradiation", Mar. 1984, The Journal of Immunology, vol. 132, No. 3 pp. 1276-1281.*

(Continued)

*Primary Examiner* — Boniface N Nganga
(74) *Attorney, Agent, or Firm* — Quarles & Brady LLP

(57) ABSTRACT

Methods and devices for suppressing clinical symptoms of multiple sclerosis (MS) by irradiating a subject exhibiting the symptoms with an effective dose of UV-containing light from a light source and detecting a suppression of the clinical symptoms of MS. In particular, the detected suppression of the clinical symptoms is disassociated from the vitamin D production within the subject.

13 Claims, 9 Drawing Sheets

(56) References Cited

U.S. PATENT DOCUMENTS

| | | | |
|---|---|---|---|
| 2008/0014176 A1* | 1/2008 | Di Mauro et al. | 424/93.7 |
| 2008/0224592 A1* | 9/2008 | Reich | C09K 11/7721 313/487 |
| 2009/0221538 A1* | 9/2009 | Hayes et al. | 514/168 |
| 2010/0121420 A1* | 5/2010 | Fiset et al. | 607/94 |
| 2011/0238140 A1 | 9/2011 | Kurkayev | |

FOREIGN PATENT DOCUMENTS

| | | |
|---|---|---|
| WO | 2008136958 A1 | 11/2008 |
| WO | 2011097383 A1 | 8/2011 |
| WO | 2013072701 A | 5/2013 |

OTHER PUBLICATIONS

Tsunoda et al., "Converting relapsing remitting to secondary progressive experimental allergic encephalomyelitis (EAE) by ultraviolet B irradiation", Nov. 2004, Journal of Neuroimmunology, vol. 160, pp. 122-134.*

Correale et al., "Immunomodulatory effects of Vitamin D in multiple sclerosis", Mar. 2009, BRAIN a Journal of Neurology, vol. 132, pp. 1146-1160.*

Chel et al., "Ultraviolet Irradiation Corrects Vitamin D Deficiency and Suppresses Secondary Hyperparathyroidism in the Elderly" Journal of Bone and Mineral Research, vol. 13, No. 8 pp. 1238-1242, Mar. 1998 (Year: 1998).*

European Patent Office, International Search Report issued in PCT/US2013/044435; dated Aug. 23, 2013.

Cantorna MT, Humpal, Winter J, & DeLuca HF (1999) Dietary calcium is a major factor in 1,25-dihydroxycholecalciferol suppression of experimental autoimmune encephalomyelitis in mice. J Nutr 129(11):1966-1971.

Becklund BR, Severson KS, Vang SV, & DeLuca HF (2010) UV radiation suppresses experimental autoimmune encephalomyelitis independent of vitamin D production. Proc Natl Acad Sci USA 107(14):6418-6423.

Hauser SL, et al. (1984) Prevention of experimental allergic encephalomyelitis (EAE) in the SJL/J mouse by whole body ultraviolet irradiation. J Immunol 132(3):1276-1281.

Cavaletti G, et al. (2004) Extracorporeal photochemotherapy reduces the severity of Lewis rat experimental allergic encephalomyelitis through a modulation of the function of peripheral blood mononuclear cells. J Biol Regul Homeost Agents 18(1):9-17.

Agranoff BW & Goldberg D (1974) Diet and the geographical distribution of multiple sclerosis. Lancet 2(7888):1061-1066.

Runia TF, Hop WC, de Rijke YB, Buljevac D, & Hintzen RQ (2012) Lower serum vitamin D levels are associated with a higher relapse risk in multiple sclerosis. Neurology 79(3):261-266.

Lemire JM & Archer DC (1991) 1,25-dihydroxyvitamin D3 prevents the in vivo induction of murine autoimmune encephalomyelitis. J Clin Invest 87(3):1103-1107.

Cantorna MT, Hayes CE, & DeLuca HF (1996) 1,25-Dihydroxyvitamin D3 reversibly blocks the progression of relapsing encephalomyelitis, a model of multiple sclerosis. Proc Natl Acad Sci USA 93(15):7861-7864.

Meehan TF, Vanhooke J, Prahl J, & Deluca HF (2005) Hypercalcemia produced by parathyroid hormone suppresses experimental autoimmune encephalomyelitis in female but not male mice. Arch Biochem Biophys 442(2):214-221.

Wang Y, Marling SJ, Zhu JG, Severson, KS & DeLuca HF (2012) Development of experimental autoimmune encephalomyelitis (EAE) in mice requires vitamin D and the vitamin D receptor. Proc Natl Acad Sci USA 109(22):8501-8504.

PCT International Search Report and Written Opinion, PCT/US2011/023608, dated Mar. 23, 2011, 13 pages.

European Patent Office, Extended European Search Report, Application No. 11740357.6, dated Sep. 16, 2013, 6 pages.

European Patent Office, Communication, Application No. 11740357.6, dated May 20, 2014, 4 pages.

European Patent Office, Communication, Application No. 11740357.6, dated Dec. 9, 2014, 3 pages.

European Patent Office, Communication, Application No. 13733128.6, dated Mar. 20, 2017, 4 pages.

European Patent Office, Communication, Application No. 13733128.6, dated Oct. 17, 2017, 3 pages.

European Patent Office, Extended European Search Report, Application No. 17204747.4, dated Apr. 16, 2018, 6 pages.

* cited by examiner

METHOD FOR TREATING MULTIPLE SCLEROSIS

CROSS-REFERENCE TO RELATED APPLICATIONS

This application claims the benefit of U.S. Provisional Patent Application No. 61/663,401, filed Jun. 22, 2012, and is a Continuation-In-Part of U.S. Ser. No. 13/576,253, filed Jul. 31, 2012, which is the national stage application of PCT/US2011/023608, filed Feb. 3, 2011 (now published as WO 2011/097383), which claims the benefit of U.S. Provisional Patent Application No. 61/301,820, filed Feb. 5, 2010. Each application is incorporated by reference herein in its entirety for all purposes and, in particular, to provide description of system and method for irradiation of a subject with UV light.

STATEMENT REGARDING FEDERALLY SPONSORED RESEARCH OR DEVELOPMENT

Not applicable.

BACKGROUND

Multiple Sclerosis (MS) is a chronic autoimmune disease characterized by inflammation, demyelination and axonal degeneration of central nervous system [1]. The prevalence of MS is inversely related to the distance from the equator in both hemispheres [2]. As a result, it has been assumed that the incidence of MS is inversely related to ultraviolet radiation exposure (UVR). UVR is also well known to produce vitamin D from 7-dehydrocholesterol (7-DHC) in skin [3]. Therefore, it was further assumed that the protection from MS by UVR is through vitamin D production [4]. The studies with supplemental vitamin D as a potential therapy of MS are ongoing [5, 6]. However, Becklund et al. demonstrated that continuous UVR suppression of experimental autoimmune encephalomyelitis (EAE) is independent of vitamin D production [7], a finding confirmed by other recent studies [8, 9]. Of considerable importance is that deficiency of vitamin D suppresses rather than increases incidence and severity of EAE [10-12]. Further, the suppression of EAE by 1α,25-dihydroxyvitamin $D_3$ (1,25-(OH)$_2D_3$) results from the hypercalcemia caused by 1,25-(OH)$_2D_3$. Low calcium diets essentially eliminates the ability of 1,25 (OH)$_2D_3$ to suppress EAE [13]. These findings force a reexamination of the idea that vitamin D production mediates the relationship between UV light and MS. In addition, deletion of the VDR gene essentially protects against EAE [12].

A number of genetic and environmental factors are thought to influence MS development. Solar radiation is considered to be one of such factors. For example, a recent study demonstrated that MS relapse rates are lower in the summer than in the winter, suggesting UV exposure may be a contributing factor in relapses [35]. Furthermore, experiments conducted in the experimental autoimmune encephalomyelitis (EAE) animal model of MS have demonstrated that seven-day pretreatment with UVR prevents disease induction in SJL mice [25].

Solar UV is composed of three different wavelength bands: UVC (100-280 nm), UVB (280-320 nm), and UVA (320-400 nm) [14]. The biological action of UVC is usually neglected because it is totally absorbed in the stratospheric ozone before reaching the earth. UVB and UVA are considered as the two major components of UVR affecting health and disease. UVR causes both deleterious and beneficial effects. The shorter wavelength (below 300 nm) of UVB causes erythema or skin injury [15] and increases the risk of carcinoma in the skin through a series of photochemical effects (DNA damage, cis-UCA formation, immunosuppression) [16-18]. The longer wavelength of UVB (300-315 nm) has less erythematic effect and lower risk of carcinogenesis [9]. UVA has a deeper penetration into the tissue than UVB and causes DNA damage indirectly through the formation of reactive oxygen species (ROS) [19]. The contribution of UVA to carcinogenesis is unclear. It was shown that UVB but not UVA is required for the pathogenesis of melanoma [20].

Irrespective of its harmful effects, UVR has been used for the treatment of several human diseases and is known as phototherapy. Broad band UVB (BB-UVB), narrow band UVB (NBUVB), broad band UVA (BB-UVA) and long wavelength UVA-1 emitted by different fluorescent lamps have been used in phototherapy for a variety of inflammatory skin diseases, such as psoriasis, vertigo, atopic dermatitis [21-23]. Phototherapy is considered as a safe and effective therapy with the proper dose. NB-UVB is superior to BB-UVB for psoriasis therapy providing higher efficacy and fewer side effects. UVB (270-300 nm) radiation results in the conversion of 7-DHC to form pre-vitamin D that isomerizes to vitamin $D_3$ [3]. Vitamin $D_3$ is then converted in the liver to the circulating form, 25-hydroxyvitamin $D_3$ (25-(OH)$D_3$). Measurement of 25(OH)D3 is used to assess the vitamin D status of patients [2]) but must be converted in the proximal tubules of the kidney to the active or hormonal form, i.e. 1α,25-dihydroxyvitamin $D_3$ (1,25-(OH)$2D_3$) [3].

Avoiding UVR exposure may reduce the risk of various skin cancers, it could inadvertently increase the risk of developing autoimmune diseases such as MS. Therefore, a need exists for a method of treating and preventing MS by administering light emitting radiation, including UVR, without the dangerous and unpleasant side effects.

SUMMARY OF THE INVENTION

Embodiments of the invention address methods for irradiating a subject with an effective dose of a narrow band of UV light that suppresses MS.

Specifically, one embodiment of the present invention provides a method for suppressing clinical symptoms of multiple sclerosis (MS) in a subject, the method comprising: (a) irradiating the subject with an effective first dose of light from a light source; and (b) detecting a suppression of the clinical symptoms in the subject.

In one specific embodiment, the irradiating includes irradiating the subject with the effective first dose of light having energy density of at least 2.5 kJ/m$^2$. Preferably, the first dose is effective to suppress multiple sclerosis symptoms and the light is characterized by a wavelength within a range from about 290 nm to about 320 nm. More preferably, the light has a wavelength between about 300 nm and about 315 nm.

In another specific embodiment, the detecting includes detecting of one or more of a the following: a delay of onset of MS symptoms, a reduction of peak of severity of MS symptoms, or a decrease of the cumulative disease index (CDI).

Another embodiment of the present invention provides a computer program product for use on a computer system for irradiating a subject with light from a light source and detecting changes in clinical symptoms of multiple sclerosis (MS) in the subject. Such computer program product comprises a computer usable tangible medium having computer readable program code thereon, wherein the computer readable program code includes: (a) program code for pre-setting parameters of irradiation with light from the light source; and (b) program code for operating the light source such as to irradiate the subject with a dose of light from the light source.

In one specific embodiment, the dose has pre-set parameters including at least one of (i) a wavelength within a first spectral range from about 290 nm to about 320 nm and radiant energy density of at least 2.5 kJ/m$^2$, and (ii) a wavelength within a spectral range from about 300 nm to about 315 nm.

Another yet embodiment of the present invention provides a computer program product for use on a computer system for irradiating a subject having multiple sclerosis (MS) with light from a light source. Such computer program product comprises a computer usable tangible medium having computer readable program code thereon, which, when loaded into the computer system, establishes an apparatus, implemented in the computer system, the apparatus comprising: (a) at least an input for receiving a set of input data representing parameters of irradiation, with the light, prescribed to the subject; and (b) a processor determining at least one of components of the light source and location of said components based on the received set of energy data.

In another embodiment the present invention is a device for use in the method of the present invention. Preferably the parameters include one or more of (i) a light source with a wavelength within a first spectral range from about 290 nm to about 320 nm and radiant energy density of at least 2.5 kJ/m$^2$, and (ii) a light source with a wavelength within a spectral range from about 300 nm to about 315 nm. In addition, the apparatus may include an output, in which appears a display of results of the exposure.

DESCRIPTION OF THE INVENTION

Figure 1:
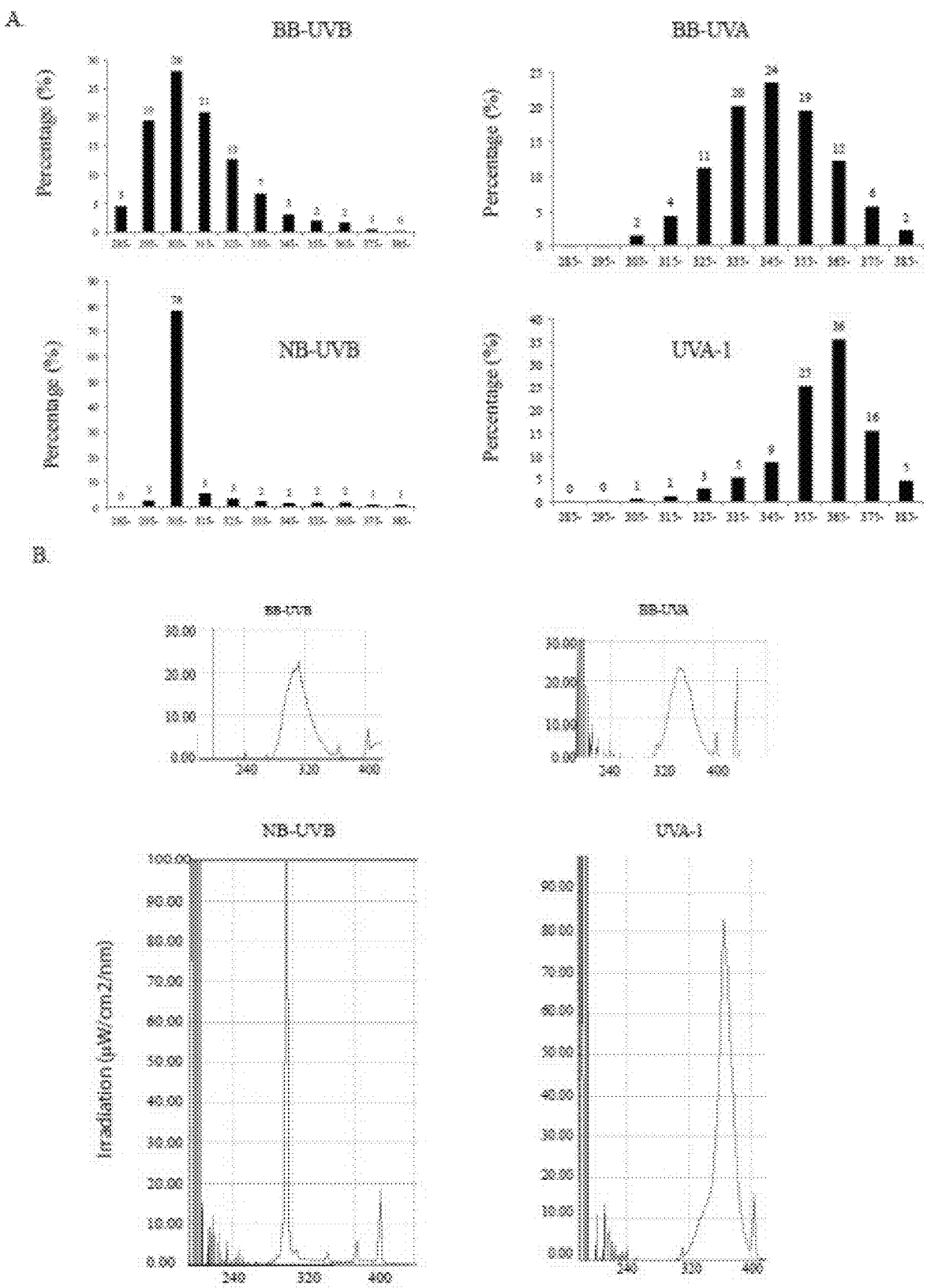
FIGS. 1A and 1B are the percent energy distribution as a function of wavelength among UV lamps used. The intensity of radiation was measured by spectroradiometer RPS900 between 285-400 nm. The percentage was calculated as intensity from every 10 nm divided by the total intensity (280-400 nm). The graph was made by the percentage of every 10 nm wavelengths. A. BB-UVB (280-330 nm: contained 86% of total energy); NB-UVB (peak at 311 nm: contained 78% of total energy); BB-UVA (300-400 nm: 100% of total energy); UVA-1 (340-400 nm: 91% of total energy). B. Plot of irradiation intensity vs. wavelength for each lamp used.

Although the exact cause of multiple sclerosis (MS) is unknown, a number of genetic and environmental factors are thought to influence MS susceptibility. One potential environmental factor is sunlight and the subsequent production of vitamin D. A number of studies have correlated decreased exposure to ultraviolet radiation (UVR) and low serum 25-hydroxyvitamin D$_3$ (25(OH)D$_3$) levels with an increased risk for developing MS.

We have demonstrated the ability of UVR to suppress disease in the EAE model of MS and allowed to assess the effect of UVR on serum 25(OH)D3 and calcium levels. These results indicated that repeated treatment with UVR, such as daily treatment, for example, dramatically suppresses clinical signs of EAE. More importantly, such suppression was associated with only a modest, transient increase in serum 25(OH)D3 levels which were insufficient to suppress EAE independent of UVR treatment. These results also suggest that UVR is likely suppressing disease independent of vitamin D production and that vitamin D supplementation alone may not replace the ability of sunlight to reduce MS susceptibility. Identification of a subject or patient appropriate for treatment of MS symptoms can be carried out based on standardized diagnostic criteria widely used by practicing physicians, specially in the first stages of the disease, such as the so-called Schumacher and Poser criteria [36-38], or the McDonald criteria, which focus on a demonstration with clinical, laboratory and radiologic data of the dissemination of MS lesions in time and space [36, 39, 40].

The most commonly used diagnostic tools for MS are neuroimaging, analysis of cerebrospinal fluid and evoked potentials. In a positive diagnosis, magnetic resonance imaging (MRI) of the brain and spine shows areas of demyelination (lesions or plaques). Gadolinium administered, as a contrast agent, to a patient with MS typically localizes in these "hot spots" or lesions, and can be easily identified with the use of MRI. The MRI of the lesions is one of the most efficient methods of diagnosing MS. Measuring the development of new lesions is also a critical and efficient method of monitoring the progression of MS.

Alternatively, MS can be diagnosed with other known methods. For instance, an MS patient may respond less actively to stimulation of the optic nerve (which may be examined using visual and sensory evoked potentials) and sensory nerves due to demyelination of these nerve pathways [41]. Chronic inflammation of the central nervous system can be demonstrated by an analysis of cerebrospinal fluid. The cerebrospinal fluid is tested for oligoclonai bands, which are present in 75-85% of people with MS [39,42].

Three laboratories have demonstrated that EAE can be suppressed by BB-UVB [7, 25, 26]. However, the active wavelengths in this suppression are unclear. The embodiments of the invention as shown in the Examples below illustrated that UVB (300-315 nm) is responsible for the suppression of EAE by BB-UV and this wavelength does not increase serum 25(OH)D3 or alter serum calcium.

Briefly, embodiments of the invention address methods and devices for irradiating a subject with an effective dose of UV light, which dose is chosen to produce substantially low clinical score representing the results of UV irradiation, and computer program products and devices configured to facilitate the operation of the system and/or the implementation of steps of the method.

Certain terms used to describe the embodiments above, as well as in the specification and claims, have meanings according to the definitions provided below, unless context requires otherwise.

"A subject" according to the embodiments of the invention includes, for example, the identified MS patient, who can be irradiated or illuminated with light from an appropriate light source.

The term "light", as used herein, encompasses electromagnetic radiation at wavelengths visible to a human eye as well as that within an ultraviolet (UV) and near-infrared (near-IR) portions of the spectrum.

The term "light source" generally refers to single or multiple mechanisms or systems serving as a source of illumination inclusive of a light emitter and optical elements that may gate or shape the illumination. Thus, for example, a reflective surface such as a mirror redirecting at least a portion of light incident upon it, or a photorefractive element such as a lens, or a spectral filter operating either in transmission or reflection that is illuminated with the light from the light emitter is included within the meaning of a light source". A light source may be used, e.g., for illumination of the MS patient.

Specifically, one embodiment of the present invention provides a method for suppressing clinical symptoms of multiple sclerosis (MS) in a subject, the method comprising: (a) irradiating the subject with an effective first dose of light from a light source; and (b) detecting a suppression of the clinical symptoms in the subject.

In one specific embodiment, the irradiating includes irradiating the subject with the effective first dose of light having energy density of at least 2.5 kJ/m$^2$. In a preferred embodiment, at least 50%, 60%, 70%, 80% or 90% of the patient's skin is exposed to the treatment.

Preferably, the first dose is effective to suppress multiple sclerosis symptoms and the light is characterized by a wavelength within a range from about 290 nm to about 320 nm. More preferably, the light has a wavelength between about 300 nm and about 315 nm. Most preferably, the 300 nm to 315 nm band is at least 90%, 95% or 99% of the light produced by the light source.

One embodiment of the present invention provides a method for suppressing clinical symptoms of MS in a subject having a reference level of serum calcium and a reference level of a serum 25(OH)D3. Such method includes irradiating the subject with such a first dose of light from a light source that is adapted to cause a change of a serum 25(OH)D3 level in the subject from the reference level of a serum 25(OH)D3 to a first level that is lower than a threshold level associated with suppression of the clinical symptoms. In addition, such method may include repeatedly irradiating the subject at repetition time intervals with a second dose of light from the light source. Here, the second dose and repetition time intervals are judiciously chosen as to maintain a serum 25(OH)D3 level below the threshold level. Repeatedly irradiating the subject may require, in one implementation, irradiating with the second dose for at least 10 minutes every 24 hours for seven days. Furthermore, the embodiment includes detecting a suppression of the clinical symptoms that is independent of a vitamin D production in the subject. These repeated doses may be, part of a continuous dose.

In one specific embodiment, the first dose may be further adapted to maintain the level of serum calcium within 0.5 mg/dL with respect to the reference level of serum calcium, while the second dose and repetition time intervals may be further adapted to cause variation of a serum 25(OH)D3 level by no more than 5 ng/mL. In another specific embodiment, each of the first and second doses of light is associated with UV irradiance of at least 2.5 kJ/m2 and, alternatively or in addition, with UVB irradiance of at least 2.5 kJ/m2.

In another specific embodiment, the detecting includes detecting of one or more of a delay of onset of MS symptoms, a reduction of peak of severity of MS symptoms, and a decrease of the cumulative disease index (CDI).

Another embodiment of the present invention provides a computer program product for use on a computer system for irradiating a subject with light from a light source and detecting changes in clinical symptoms of multiple sclerosis (MS) in the subject. Such computer program product comprises a computer usable tangible medium having computer readable program code thereon, wherein the computer readable program code includes: (a) program code for pre-setting parameters of irradiation with light from the light source; and (b) program code for operating the light source such as to irradiate the subject with a dose of light from the light source.

In one specific embodiment, the dose has pre-set parameters including at least one of (i) a wavelength within a first spectral range from about 290 nm to about 320 nm and radiant energy density of at least 2.5 kJ/m$^2$, and (ii) a wavelength within a spectral range from about 300 nm to about 315 nm.

Another yet embodiment of the present invention provides a computer program product for use on a computer system for irradiating a subject having multiple sclerosis (MS) with light from a light source. Such computer program product comprises a computer usable tangible medium having computer readable program code thereon, which, when loaded into the computer system, establishes an apparatus, implemented in the computer system, the apparatus comprising: (a) at least an input for receiving a set of input data representing parameters of irradiation, with the light, prescribed to the subject; and (b) a processor determining at least one of components of the light source and location of said components based on the received set of energy data.

In one specific embodiment, the present invention is a device comprising a light source optimized for the present invention. Preferred parameters include one or more of (i) a wavelength within a first spectral range from about 290 nm to about 320 nm and radiant energy density of at least 2.5 kJ/m², and (ii) a wavelength within a spectral range from about 300 nm to about 315 nm. In addition, the device may include an output, in which appears a display of results of the exposure.

In one embodiment, the present invention is a device comprising a light source that may include a light emitter generating light, whether at a predetermined wavelength or within at least one spectral band of interest, directly illuminating the patient with intensity and/or irradiance that generally depend on a mutual positioning of the light source and the patient. For example, and without loss of generality, a light emitter such as a fluorescent tube, or a mercury vapor light, or a light-emitting diode (LED), or an incandescent lamp may be used to emit UV light towards the patient. The light emitting source may be part of a blanket or fabric covering. In another embodiment, the light source may be in the form of a light panel and the patient may position himself or herself in front, underneath or on top of the light source.

According to the present invention, a preferable light source is chosen to emit light within the UV-B band (e.g., between 280-320 nm) and, more particularly, within an optimized UV-B band, defined as a spectral region between approximately 300 and 315 nm. Various levels of patient-exposure to illumination are within the scope of this invention and, in a specific embodiment, the light source should be configured to assure patient irradiance of at least 2.5 kJ/m². In another embodiment of the invention, the light source also emits non-UV light.

According to embodiments of the invention, the light emitter may be supplemented with auxiliary optical component or a plurality of components that modifies spatial distribution of light emitted by the light emitter. For example, the light source may comprise a reflector intercepting at least a portion of emitted light and redirecting it towards the subject. Such a reflector may contain a generally curved reflective surface and, in particular, may incorporate a flat mirror or an optical diffractive element such as a diffractive grating. In a specific aspect, a reflector may include a parabolic reflecting surface that at least partially collimates light emitted by the light emitter positioned at the focal point of the reflector and redirects this light towards the patient that is located at a specified distance from the light emitter.

In another aspect, the light source may contain an optical system including at least one lens that is used to deliver substantially collimated light towards the patient. In such a light source, a light emitter such as a LED may be disposed at or near the focal point of the optical system. Alternatively, an optical system including at least one lens may be configured to shape the emitted light into a non-collimated beam that is further directed towards the subject, which is located at such a distance from the light emitter at to assure the exposure of the subject to the produced illumination at specified levels of irradiance and/or intensity.

In yet another aspect, the light source may be configured so as to illuminate the subject substantially from all directions, in such an embodiment, the light source may comprise a reflector shaped generally as a three-dimensional elliptical chamber and substantially surrounding both the light emitter disposed at or near one focal point of the chamber and the subject located at another focus of the chamber. It is appreciated that, in this case, substantially ail of the emitted light will be reflected by the internal wails of the chamber towards the subject.

In a related aspect of the invention, the light source may include an emitter emitting light within a broad spectral range and at least one spectral filter intercepting the emitted light so as to filter out the light within a specific spectral band that is preferred for illumination of the subject. In one implementation where the subject should be illuminated with the UV-light, an optical filter transmitting the UV-light within the specified band (such as UV-B or UV-A) may be disposed across a collimated beam of light formed by the optical system of the light source and propagating towards the subject. A variety of known optical filters may be used for such purpose such as, for example, dichroic and multichroic filters, interference filters including thin-film filters.

The term "irradiance" is used to describe surface density of light incident on a reference surface in terms of radiant power per unit area or, alternatively, in terms of radiant energy per unit area. "Intensity" refers to spatial density of light expressed, for example, as radiant power per unit solid angle or as radiant energy per unit solid angle.

Irradiation of the subject with light from the light source of an embodiment of the invention may be generally carried out within a single time period, or repeatedly during several time-intervals, or even continuously, as required to achieve a particular level of light-exposure of the subject.

The overall length of irradiation or treatment is, preferably, defined by a degree of severity of MS exhibited by the patient. In one embodiment of the present invention, a patient may be exposed to light treatment until the most severe of his or her MS symptoms are abated or reduced. In another embodiment of the present invention, the patient may be exposed to light treatment on a daily basis for as long as relief from MS symptoms is desired.

In one embodiment of the present invention, subjects would be irradiated daily for at least 10 minutes, preferably 10-30 minutes, at a distance of at least 40 cm from the UV light source. Typically, treatment would be at least 7 days. One may wish to extend treatment either every day or every other day or every third day for the duration of the treatment. In another embodiment, patients may be irradiated with a lower dose of light but a longer, in some embodiments continuous, interval of light exposure. For example, one may wish to replace a house-hold light source with a light source capable of emitting a UV light dose suitable for the present invention.

One would monitor the patient's MS symptoms and detect a reduction or delay in these symptoms. Most preferably, the development of new lesions in the subject would be monitored on a regular (i.e., semi-annual) basis via MRI. Further symptoms that may be monitored include those selected from the group consisting of changes in sensation (hypoesthesia and paraesthesia), muscle weakness, muscle spasms, or difficulty in moving; difficulties with coordination and balance (ataxia); problems in speech (dysarthria) or swallowing (dysphagia), visual problems (nystagmus, optic neuritis, or diplopia), fatigue, acute or chronic pain, and bladder and bowel difficulties. Cognitive impairment of varying degrees and emotional symptoms of depression o unstable mood are also common. One common clinical measure of disability progression and symptom severity is the Expanded Disability Status Scale or EDSS.

"Suppression" in MS symptoms is defined to include any significant reduction of MS symptoms. "Delay" of MS symptoms, on the other hand, is defined to include a significant delay in the development of MS symptoms. For instance, in one embodiment, after daily treatment with the method of the present invention, one would expect to see at least 30% reduction in the symptoms associated with the lesions on the patient's nervous system. With fewer lesions, one would expect less corresponding symptoms, including a delay in, for instance, the appearance of episodic acute periods of worsening (i.e. relapses, exacerbation, bouts, attacks, or flare ups). These episodic periods are also susceptible to reduction and delay and are within the scope of the present invention.

Figure 6:
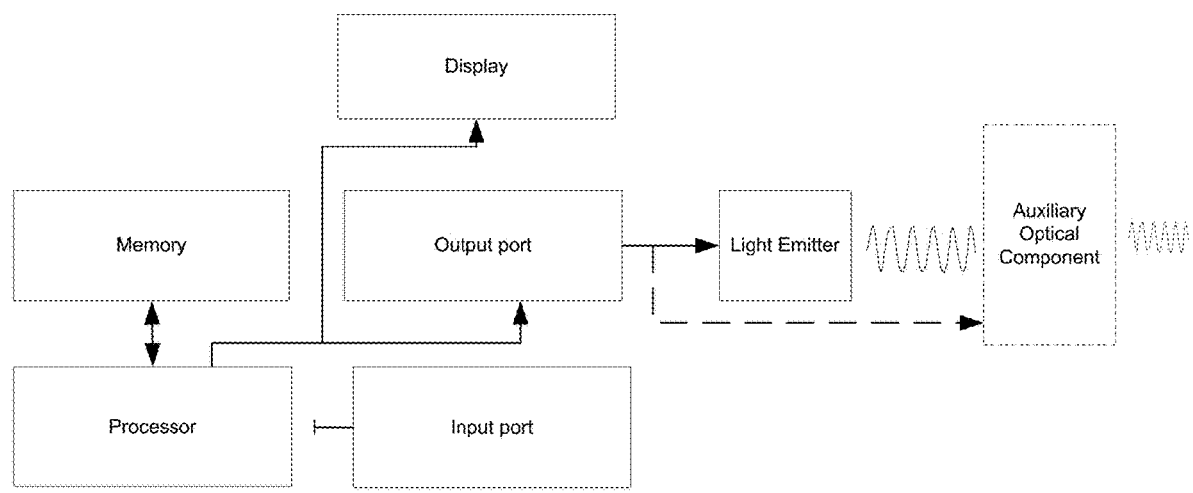
FIGS. 6, 8, and 9 illustrate computerized devices for applying the treatments discussed with reference to FIGS. 1-5B.

It is appreciated that implementation and/or operation of the embodiment of the invention, including but not limited to optional calibration and/or tuning of the employed light source, irradiation of the subject under test, detection of changes in clinical parameters, collection of data representing a process of irradiation and/or detected clinical parameters, and establishing an apparatus implemented in a computer system—is preferably enabled with the use of a processor controlled by instructions stored in a memory. Referring to FIG. 6, a block diagram of an exemplary processor-controlled device for providing UV light treatments as described herein is shown. Here, a processor 20, which can be a microprocessor, microcontroller, or similar devices, is communicatively coupled to a memory 22. The memory 22 may include random access memory (RAM), read-only memory (ROM), flash memory or any other memory, or combination thereof, suitable for storing control software or other instructions and data. An input port 24 can receive input commands from a user interface (not shown) such as a keyboard, touch screen, infrared or wireless communications device, or similar devices. The processor 20 receives input commands from a user, and provides commands to an output port 28 which can drive a light emitter 12 to provide irradiation for use in the treatment. The output port 28 can, for example, comprise a switch for switching power to the light emitter 12, or a switching power supply, digital to analog convertor, or other device for selectively providing a selected level of power to the light emitter 12, or other similar devices. The processor can also be connected to a display 26 providing access for the user to view stored images and clinical data, and to verify scheduling, as described below. Although the components shown here may be constructed as a specific device for controlling the described treatment, in some applications standardized desktop, laptop, or other computerized devices can be used. For example, in some embodiments the light emitter 12 could be coupled to a USB port or other output device on a computer which could be selectively switched on by internal software to activate the light emitter 12. Although a processor 20, memory 22, input port 24 and output port 28 are shown here as separate components, it will be apparent to those of skill in the art that various combinations of these devices can be combined in a single component.

In some embodiments, a bracket 34 may be provided to mount auxiliary optical components 14 adjacent the output of the light emitter 12. The auxiliary optical components 14 can filter, collimate, diffract, reflect, or otherwise modify light waves emitted from the light emitter 12, as described above. The mounting bracket 30 may be stationary, or, in some applications my include a motor or other motion control device (not shown) in communication with the processor to selectively drive one or more auxiliary optical component in position adjacent the light emitter 12. In some applications, a number of auxiliary optical components can be mounted to the bracket and the processor 20 can be programmed to selectively drive the auxiliary optical components 14 into position adjacent the light emitter 12.

Referring still to FIG. 6, the memory 22 can store, for example, proposed treatment protocols and timing parameters, which can be retrieved by a user and used to activate the light emitter 12 in a treatment protocol. The memory 22 can also store a patient database including, for example, patient identification, corresponding historical treatment data, future scheduled timed treatment protocols, auxiliary optical equipment used, MRI images for use in comparative treatment analysis, and serum calcium and serum 25(OH)D3 levels. The memory can also store timing parameters for real-time treatment protocols using the light emitter 12, as described below. In some applications, the processor 20 can be in communication with a network, such as a wired or wireless LAN or WAN, or the internet, and can be programmed to generate notifications such as emails, text messages, or other electronic messages for notifying a medical practitioner or a patient that a treatment time is scheduled.

When used in treatment, the processor 20 can prompt a user to identify the patient for storage in or retrieval from a database in memory 20. Next, the processor can prompt the user to select a stored treatment protocol, or simply to activate the light emitter 12 to provide a timed application of light to the patient. If the user chooses to select a stored treatment, the processor can prompt the user to select a treatment from memory 20, and can provide instructions for application of the treatment. If the user instead chooses to apply a timed treatment, the processor can, for example, prompt the user to enter a treatment time, and then activate the light emitter for the selected time. Alternatively, the processor 20 can activate the light emitter 12 and wait for a signal from the user to stop treatment. The display 26 can illustrate an elapsed time during treatment. After a treatment is complete, the user can be prompted to store data, including the date and time of the treatment, elapsed time of the light application, identification of the light used in the treatment, and other data with data identifying the patient in the database. The processor 20 can also provide a future schedule for the application of the next treatment in a series. The processor 20 can also provide access for the user to upload images or clinical data to the memory 22 for comparative analysis during an on-going treatment protocol. Statistical analyses of the stored data can also be performed by the processor 20.

Figure 7:
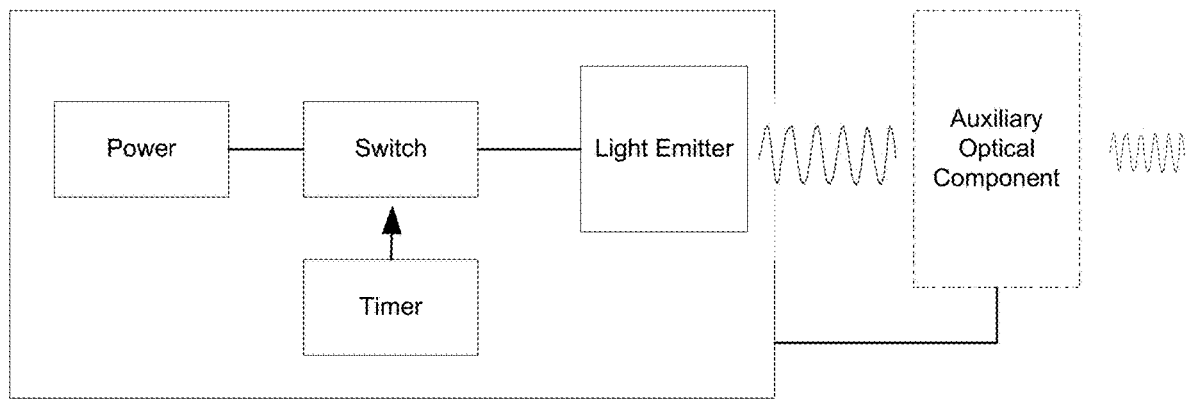
FIG. 7 illustrates an alternate embodiment of a device for applying timed treatments as discussed with reference to FIGS. 1-5B.

Referring now to FIG. 7, in alternate embodiments, the light emitter 12 can be provided in a housing 11 with a dedicated timer 30 configured to selectively activate a switch 32 for the application of power to the light emitter 12. The timer 30 can be a programmable timer, or a timer dedicated to activate the switch 32 for known, predetermined time periods. A bracket 34 can be coupled to the housing 11 and configured for mounting an auxiliary optical component 14 adjacent the light emitter 12, as discussed above.

Figure 8:
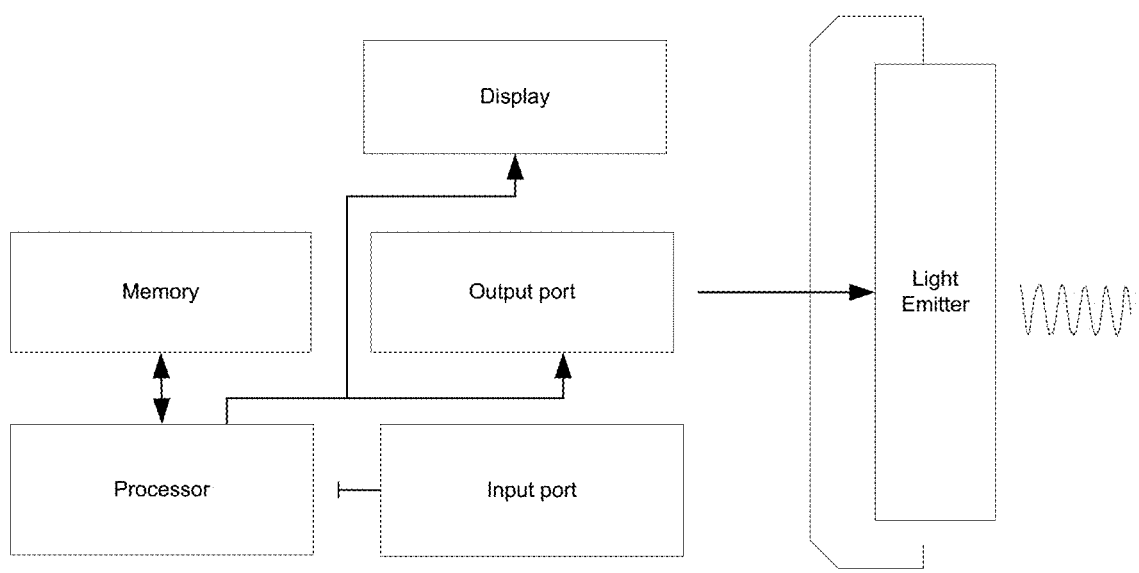
Figure 9:
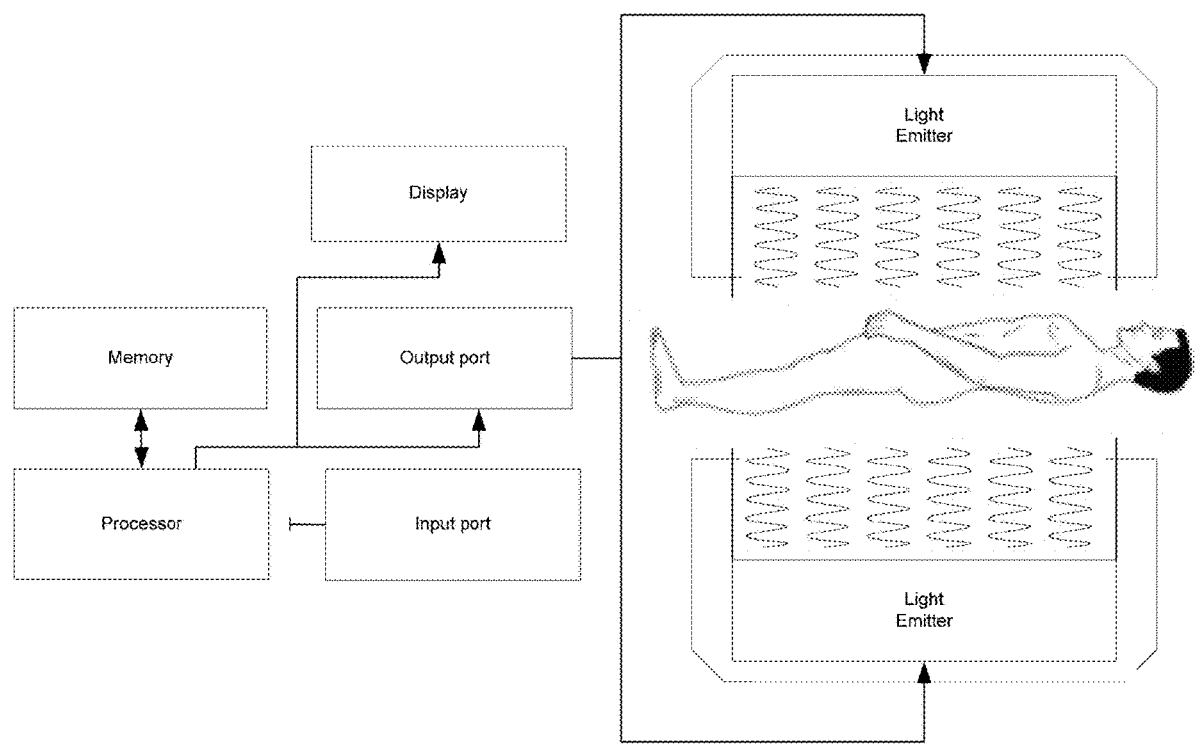

Referring now to FIG. 8, in one exemplary embodiment, the light emitter 12 can be mounted in a housing 15 coupled to a circuit of the type described with reference to FIGS. 6 and 7 by way of a cable or other device. The cable can be flexible, allowing a user to position the light emitted from the light emitter 12 at a selected location, or to position the light emitter 12 in a reflective chamber or other device for application of light to the patient. Referring now also to FIG. 9, in another exemplary embodiment, one or more light emitters 12 and 13 can also be mounted in a chamber comprising an upper and a lower housing 32 and 34 sized and dimensioned to receive a patient therebetween. Sides of the enclosed housing can be coupled together and sealed with a gasket to prevent leakage of light. As described above, the light emitters 12 and 13 can also be mounted in a flexible housing such as a blanket or meshed surface that can be wrapped around the patient for application of light.

Various functions, operations, decisions, etc. of all or a portion of any embodiment of the invention, therefore, may be implemented as computer program instructions, software, hardware, firmware or combinations thereof. Those skilled in the art should also readily appreciate that instructions or programs defining the elements of an embodiment of the present invention may be delivered to a processor in many forms, including, but not limited to, information permanently stored on non-writable storage media (e.g. read-only memory devices within a computer, such as ROM, or devices readable by a computer I/O attachment, such as CD-ROM o DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Each of the publications and patent documents specifically mentioned herein is incorporated by reference in its entirety for ail purposes including describing and disclosing the chemicals, instruments, statistical analyses and methodologies which are reported in the publications and which might be used in connection with the invention. All references cited in this specification are to be taken as indicative of the level of skill in the art. Nothing herein is to be construed as an admission that the invention is not entitled to antedate such disclosure by virtue of prior invention.

Also, unless defined otherwise, all technical and scientific terms used herein have the same meanings as commonly understood by one of ordinary skill in the art to which this invention belongs. For example, it should be understood that while various embodiments in the specification are presented using "comprising" language, under various circumstances, a related embodiment is also be described using "consisting of" or "consisting essentially of" language. It is to be noted that the term "a" or "an," refers to one or more, for example, "an immunoglobulin molecule," is understood to represent one or more immunoglobulin molecules. As such, the terms "a" (or "an"), "one or more," and "at least one" is used interchangeably herein.

EXAMPLES

The following examples set forth preferred predictors and methods in accordance with the invention. It is to be understood, however, that these examples are provided by way of illustration and nothing therein should be taken as a limitation upon the overall scope of the invention.

Example 1

Suppression of EAE by BB-UVB and NB-UVB
Materials and Methods.

Female C57BL/6 mice (6-8 weeks old) purchased from Jackson Labs were used in this experiment. All mice were shaved with an electric clipper on their back to receive UV radiation at one day before UVB treatment. The mice were randomly divided into the following five groups (n=12 for each group): 1) Control; 2) UVB-BB 2.5 KJ/m$^2$; 3) UVB-BB 5.0 KJ/m$^2$; 4) UVB-NB 2.5 KJ/m$^2$; 5) UVB-NB 5.0 KJ/m$^2$. A set of four FS20T12/2 Ft UVB-BB bulbs (wavelength range: 290 nm-320 nm, Amjo Corp, West Chester, Ohio) was used in UVB-BB group. An example of spectral distribution of optical output of the UVB-BB group light source(s) is shown in FIG. 1. A set of four TL20W/01 UVB 311 narrow band 2 Ft bulbs (wavelength centered at 311 nm-313 nm, Amjo Corp, West Chester, Ohio) was used in UVB-NB group. An example of spectral distribution of optical output of the UVB-NB group light source(s) is shown in FIG. 1A. "The radiation output was measured and calculated with equal intensity by using a UV radiometer equipped with a sensor the spectral sensitivity band of which falls within the UVB BB (for example, the UVP sensor band that is centered at about 302 nm), at chosen times before, in the middle of, and at the end of experiment. Mice were put into a 16-chamber Plexiglas cage individually to receive daily UV radiation from day 7 prior to immunization to day 30 after immunization. Each mouse was rotated in the different chamber to avoid uneven UV radiation in the experiment.

EAE Induction.

In this Example, the EAE mice were immunized with myelin oligodendrocyte glycoprotein peptide (MOG)$_{35-55}$. MOG$_{35-55}$ (MEVGWYRSPFSRVVHLYRNGK) was synthesized at the University of Wisconsin-Madison Biotechnology Center and purified to at least 95% by reverse-phase HPLC. MOG$_{35-55}$ was suspended in sterile PBS and emulsified with equal volume of complete Freund's adjuvant (CFA) containing 5 mg/ml inactivated *Mycobacterium tuberculosis* H37Ra (DIFCO Laboratories). Each mouse was immunized with subcutaneous injection of 100 microliter MOG$_{35-55}$/CFA emulsion (containing 200 ng MOG$_{35-55}$) and intraperitoneally injection with 200 ng of pertussis toxin (List Biological Laboratories) diluted in sterile PBS. The second booster pertussis toxin injection was given at 48 hours later. Each mouse was scored daily for clinical signs of EAE using the following scale: 0, no clinical disease; 1, loss of tail tone; 2, unsteady gait; 3, hind limb paralysis; 4, forelimb paralysis; 5, death.

TABLE 1

Suppression of UVB Broadband and UVB Narrowband on EAE

| | Incidence | Day of onset | Mean Severity | CDI |
| --- | --- | --- | --- | --- |
| Control | 92% (11/12) | 10 ± 1 | 2.9 ± 0.7 | 55 ± 15 |
| UVB-NB 2.5 KJ/m$^2$ | 92%(11/12) | 19 ± 4 * | 2.3 ± 1.0 | 29 ± 17 * |
| UVB-NB 5.0 KJ/m$^2$ | 67% (8/12) | 20 ± 4 * | 1.5 ± 1.1 * | 16 ± 17 * |
| UVB-BB 2.5 KJ/m$^2$ | 83% (10/12) | 16 ± 4 * | 1.9 ± 1.0 * | 28 ± 18 * |
| UVB-BB 5.0 KJ/m$^2$ | 50% (6/12) | 22 ± 4 * | 0.9 ± 1.1 * | 9 ± 11 * |

Statistical Analysis.

In reference to FIG. 1B experimental data (representing efficiency of irradiation of subjects with UV light form light sources of the UVB-BB and UVB-NB groups) were expressed as mean±standard deviation (SD). Onset was calculated by averaging the first day when clinical signs appeared 1.0 for continuous 2 days. Mean severity was determined by averaging the clinical scores during the entire experiment. The CDI was calculated by summing the clinical scores in each animal and divided by the number of mice per group. Statistical analyses were performed using the two-tailed Fisher exact probability test for incidence, the Mann-Whitney nonparametric u test for clinical scores, and the unpaired Student t test for all other measurements. A value of P<0.05 was considered statistically significant.

Example 2

Suppression of EAE by BB-UVB, NB-UVB and BB-UVA

Materials and Methods

Animals and Diet.

Female C57BL/6 mice (6-8 weeks old) purchased from Jackson Laboratory were fed a standard lab diet chow 5008 (Purina Mills, Richmond, Ind.) and maintained in the Department of Biochemistry's vivarium. The mice were exposed to 12 h light-dark cycles. All procedures were approved by the Research Animal Resources Committee of the College of Agricultural & Life Sciences, University of Wisconsin-Madison.

UVB and UVA Radiation Treatment.

One day before treatment, the backs of mice were shaved using an electric razor. The mice were irradiated with a bank of four filtered UV lamps that emit UV light ranging from 280 to 400 nm (Amjo Corp, West Chester, Ohio). The shorter wavelength (below 280 nm) was removed by using a cellulose triacetate filter sheet (Kodacel, Rochester, N.Y.). Four sets of UV fluorescent lamps were used as follows: 1). BB-UVB: 280-330 nm (FS20T12); 2). NB-UVB: 300-315 nm peak at 311 nm (TL20W/01); 3). BB-UVA: 300-400 nm (F72T12/BL/HO); 4). UVA-1: 340-400 nm peak wavelength at 370 nm (F20T12/BL9/HO). The radiation output was measured by placing a UV radiometer equipped with 302 nm and 365 nm sensors (UVP) at five locations, representing the positions occupied by the mice. This was confirmed using a wide band spectroradiometer RPS900 (International Light, Peabody, Mass.). To achieve equal energy intensity and the time of radiation was adjusted in the case of the different bulbs used. For actual radiation, mice were put into a 16-chamber Plexiglas cage individually and received daily UV radiation from day 7 prior to immunization to day 30 after immunization as described previously [7]. Each mouse was rotated in the chambers to assure each mouse in the group received identical radiation.

EAE Induction and Score.

Mice were immunized with myelin oligodendrocyte glycoprotein peptide $(MOG)_{35-55}$ as described previously [7]. $MOG_{35-55}$ (MEVGWYRSPFSRVVHLYRNGK) was synthesized at the University of Wisconsin-Madison Biotechnology Center and purified to ≥95% by reverse-phase HPLC. $MOG_{35-55}$ was suspended in sterile PBS and emulsified with equal volume of complete Freund's adjuvant (CFA) containing 5 mg/ml inactivated *Mycobacterium tuberculosis* H37Ra (DIFCO Laboratories, Detroit, Mich.). Each mouse was immunized with subcutaneous injection of 100 μl $MOG_{35-55}$/CFA emulsion (containing 200 μg $MOG_{35-55}$) and intraperitoneally injection with 200 ng of pertussis toxin (List Biological Laboratories, Campbell, Calif.) diluted in sterile PBS. The second booster pertussis toxin injection was given 48 h later. Each mouse was scored daily for clinical signs of EAE using the following scale: 0, no clinical disease; 1, loss of tail tone; 2, unsteady gait; 3, hind limb paralysis; 4, forelimb paralysis; 5, death.

Serum Calcium Measurement.

Blood was collected initially and at termination of the experiments. Blood samples were spun at 2,938×g for 15 min, followed by a second spin at 16,883×g for 1 min. Serum calcium levels were determined from three measurements per sample in 0.1% $LaCl_3$ by atomic absorption spectroscopy (PerkinElmer, Waltham, Mass.).

Serum 25-(OH)D3 Measurement.

Blood was collected at the initial and termination of the experiments. Serum was prepared as described above. Serum 25(OH)D3 levels were determined by using 125I-radioimmunological assay according to the manufacture's instruction (DiaSorin, Stillwater, Minn.). Radioactivity was measured with a Cobra 5002 y-scintillation counter (PerkinElmer, Waltham, Mass.).

Statistical Analysis.

Data were expressed as mean±SD. Onset was calculated by averaging the first day when clinical signs appeared ≥1.0 for two continuous days. Mean severity was determined by averaging the clinical scores during the entire experiment. The CDI was calculated by summing the clinical scores for all animals in a group divided by the number of 10 mice per group. Statistical analyses were performed using the two-tailed Fisher exact probability test for incidence, the Mann-Whitney nonparametric u test for clinical scores, and the unpaired Student's t test for all other measurements. A value of $P<0.05$ was considered statistically significant.

Results

NB-UVB Treatment Suppresses EAE Similar to BB-UVB.

In our previous studies, pretreatment with 2.5 $KJ/m^2$ UVB for seven days prevented the development of EAE in SJL/J mice immunized with mouse spinal cord homogenate (MSCH) [25]; pretreatment for 7 days followed by 2.5 $KJ/m^2$ UVB every other day for the entire experiment suppressed clinical signs of EAE in C57BL/J mice immunized with $MOG_{35-55}$ [7]. Furthermore, the suppression of EAE was found to be independent of vitamin D production [7]. To determine the most effective wavelength of UVR on EAE suppression, we chose four UV lamps that emit differing wavelengths: BB-UVB (280-330 nm); NB-UVB (300-315 nm); BB-UVA (300-400 nm); and UVA-1 (340-400 nm). The graphs made from a spectroradiometer RPS900 showed that both narrow band of UVB and UVA have comparatively selective emissions compared to the BB UVR (FIGS. 1A and 1B).

Figure 2:
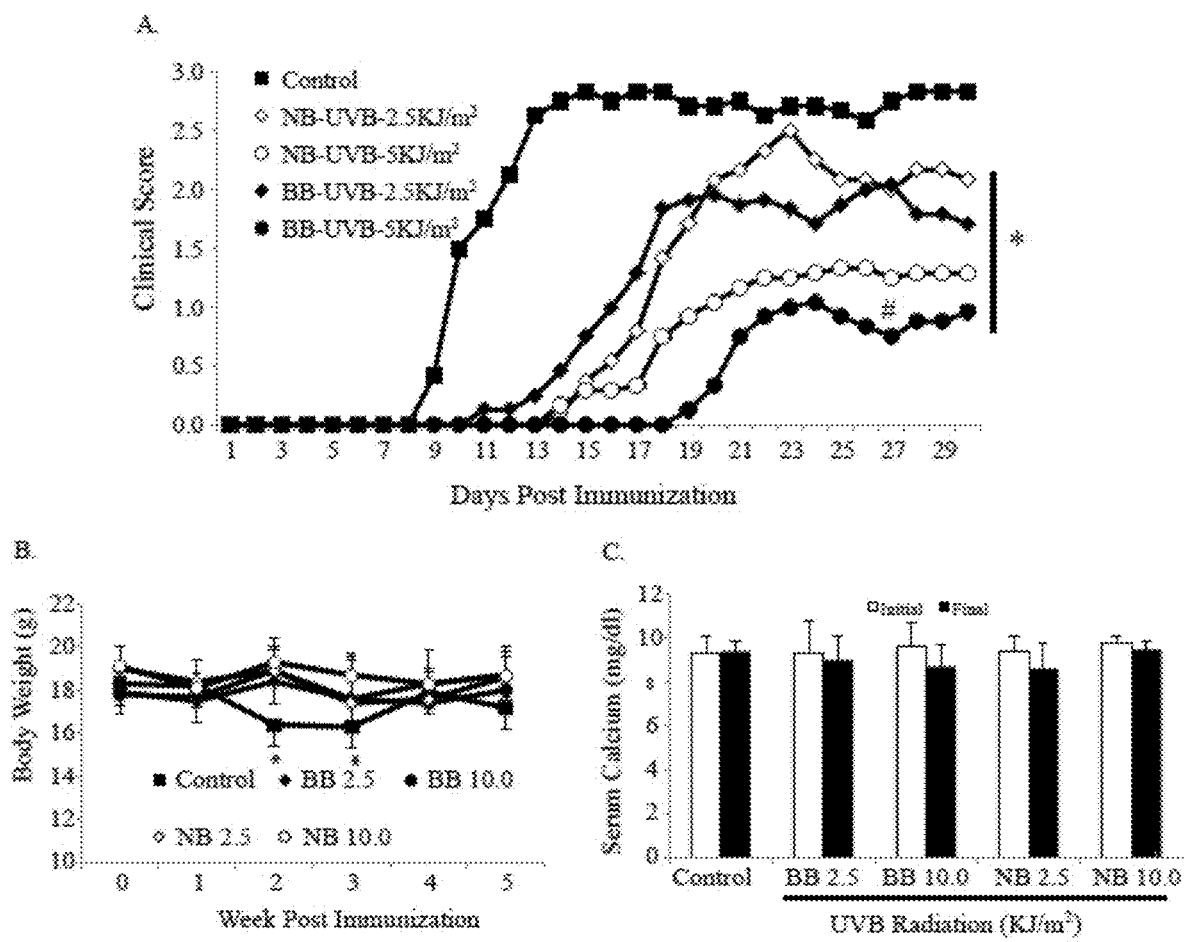
FIG. 2A shows NB-UVB irradiation equaled that of BB-UVB in suppression of EAE.
FIG. 2B illustrates the body weights of the mice in the study. 2A. Daily clinical score was the average from 12 mice. 2B. The average weekly body weight. 2C. Serum calcium was determined at the end of experiment. 2A. *$p<0.05$ vs Control. # $p<0.05$ 2.5 KJ/m$^2$ vs 5.0 KJ/m$^2$. 2B. *$p<0.05$ vs week 0.

The severity of EAE (average daily clinical score, mean score and CDI) was depressed after NB-UVB and BB-UVB radiation at both ~2.5 $KJ/m^2$ and ~5.0 $KJ/m^2$ (Table 2; FIG. 2). The onset day of EAE was delayed significantly at both low dose (~2.5 $KJ/m^2$) and medium dose (~5.0 $KJ/m^2$) (Table 2; FIG. 2). There was no difference between NB-UVB and BB-UVB, suggesting that the wavelength causing the suppression is 300-315 nm. Moreover, there was a dose-dependent response with NB-UVB and BB-UVB treatment (FIG. 2A). Body weight was measured weekly during the entire experiment. Both BB-UVB and NB-UVB did not affect body weight, indicating tolerance of UVB radiation (FIG. 2B). The significant decrease of body weight in the control group is likely the result of progressive EAE. Serum calcium was unchanged in any group (FIG. 2C).

TABLE 2

Suppression of EAE by BB-UVB and NB-UVB

| Treatment | Incidence | Day of onset | Mean Severity | CDI |
|---|---|---|---|---|
| Control | 92% (11/12) | 10 ± 1 | 2.9 ± 0.7 | 55 ± 15 |
| BB-UVB 2.5 $KJ/m^2$ | 83% (10/12) | 16 ± 4* | 1.9 ± 1.0* | 28 ± 18 |
| BB-UVB 5.0 $KJ/m^2$ | 50% (6/12) | 22 ± 4* | 0.9 ± 1.1* | 9 ± 11 |
| NB-UVB 2.5 $KJ/m^2$ | 92% (11/12) | 19 ± 4* | 2.3 ± 1.0 | 29 ± 17* |
| NB-UVB 5.0 $KJ/m^2$ | 67% (8/12) | 20 ± 4* | 1.5 ± 1.1 | 16 ± 17* |

*vs Control

BB-UVA Treatment Moderately Suppresses Severity of EAE.

Figure 3:
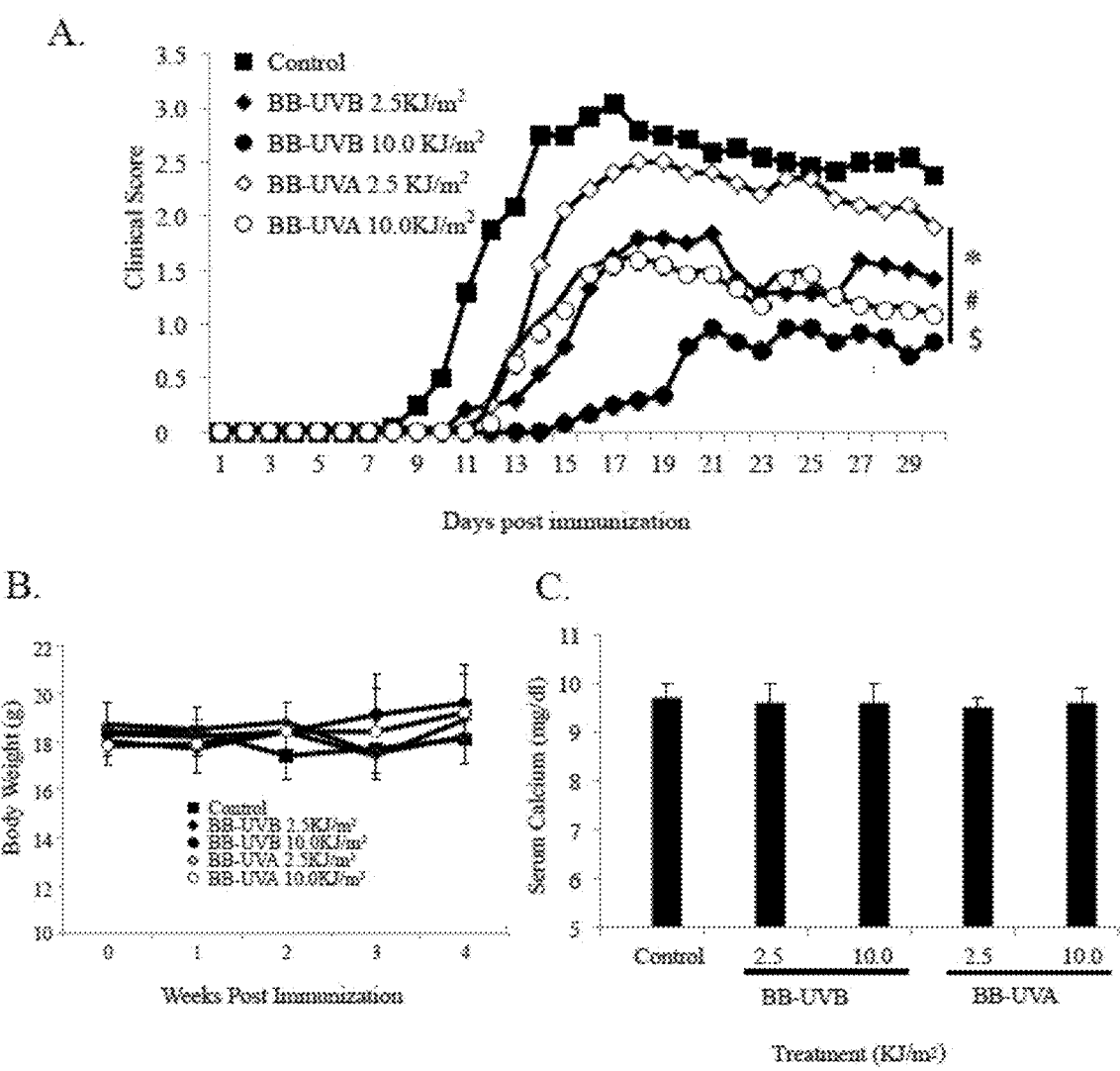
FIGS. 3A-C demonstrate that BB-UVA treatment moderately suppressed EAE severity. Mice received daily BB-UVB or BB-UVA treatment between 7 days prior to the immunization and 30 days after immunization. Clinical score was measured daily for 30 days after immunization. A. Average daily clinical score in BB-UVB and BB-UVA groups after immunization; B. Body weight was measured weekly during the entire experiment; C. Serum calcium was measured at the termination of experiment. * $p<0.05$ vs Control; # $p<0.05$ 2.5 KJ/m$^2$ vs 10.0 KJ/m$^2$; *$p<0.05$ UVB vs UVA.

BB-UVA slightly suppresses EAE severity at a low dose of ~2.5 KJ/m² and causes a decrease in EAE severity at high dose of 6~10.0 KJ/m². This equals the effect of BB-UVB at a low dose of ~2.5 KJ/m² (FIG. 3A and Table 3). Since there was overlap between BB-UVA and BB-UVB from 305-365 nm, we further used UVA-1 which has minimal overlap with UVB (FIGS. 3B and C).

Figure 4:
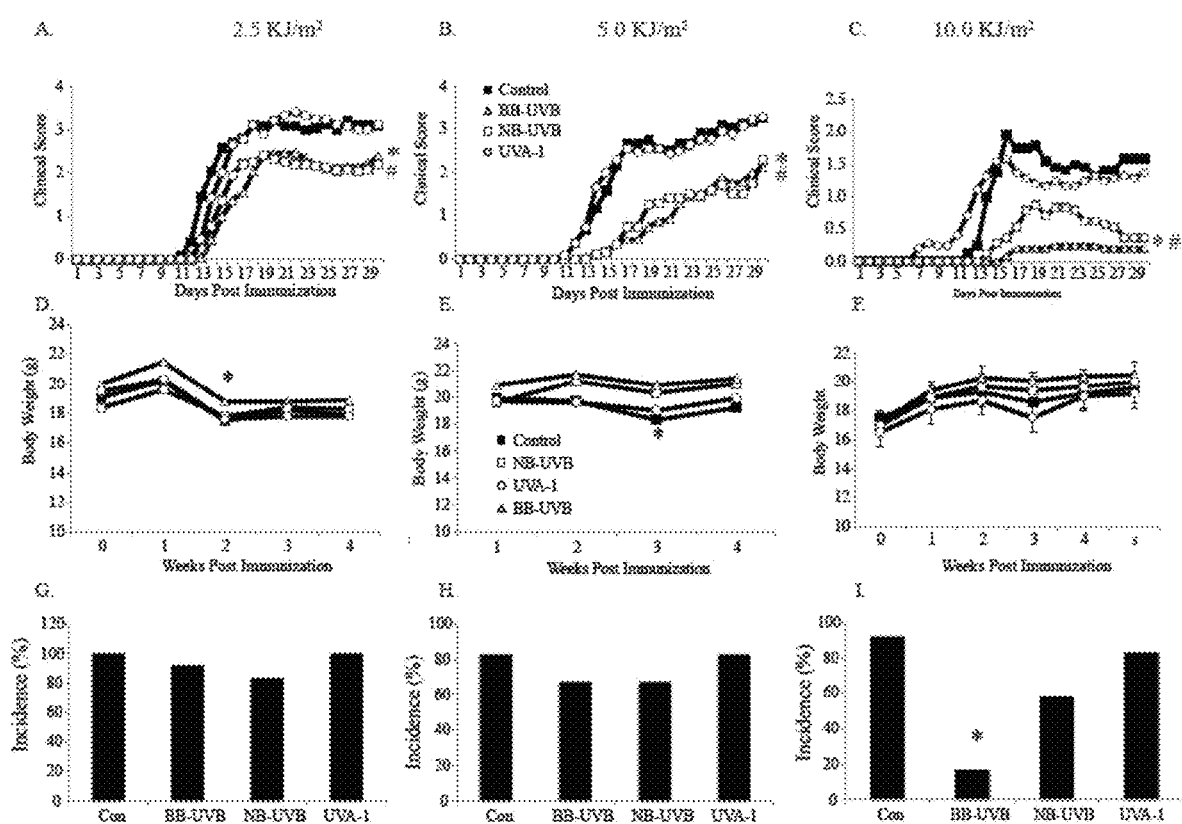
FIGS. 4A-I demonstrate that UVA-1 failed to suppress EAE at low, medium and high dose. The mice received equal daily radiation from BB-UVB, NB-UVB and UVA-1 at low (~2.5 KJ/m$^2$), medium (~5.0 KJ/m$^2$) and high (~10.0 KJ/m$^2$) doses from d−7 to d+30. UVA-1 treatment had no effect on EAE at any dose tested, while both BB-UVB, NB-UVB were clearly effective; D-F. Weekly weight record of mice. G. EAE incidence of EAE in mice given ~2.5 KJ/m$^2$; H. ~5.0 KJ/m$^2$; I.~10.0 KJ/m$^2$. *$P<0.05$ vs Control; # $P<0.05$ vs UVA-1.

UVA-1 did not suppress EAE progression at any dose. In contrast, BB-UVB and NBUVB consistently suppressed EAE in a dose-dependent manner (FIG. 4A-C). Body weight decreased at the end of experiment in UVA-1 group (FIG. 4D-F). In particular, UVA-1 also did not change incidence of EAE, while BB-UVB did (FIG. 4G-I).

Figure 5:
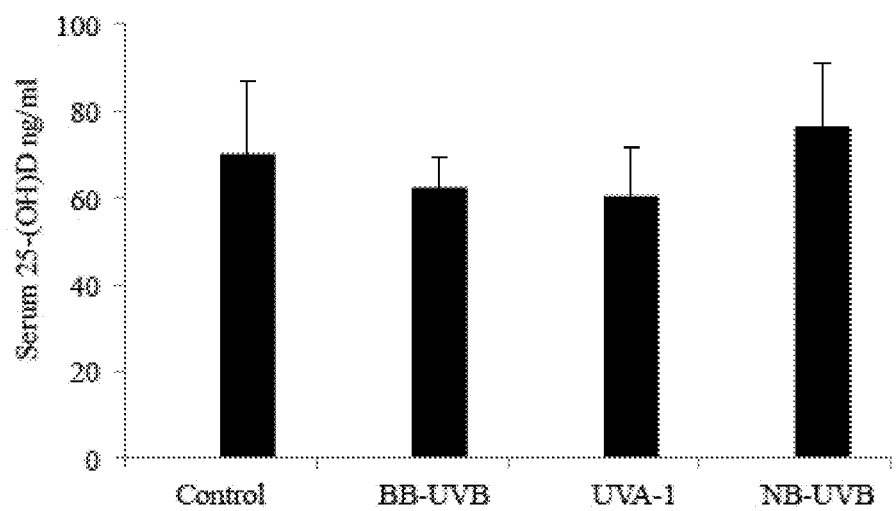
FIGS. 5A and 5B show that serum 25(OH)D3 concentration following treatment with: A. BB-UVB, NB-UVB and UVA-1 at ~2.5 KJ/m2; B. BB-UVB, NB-UVB and BB-UVA at ~10.0 KJ/m2. *$p<0.05$ vs Control.
Figure 5:
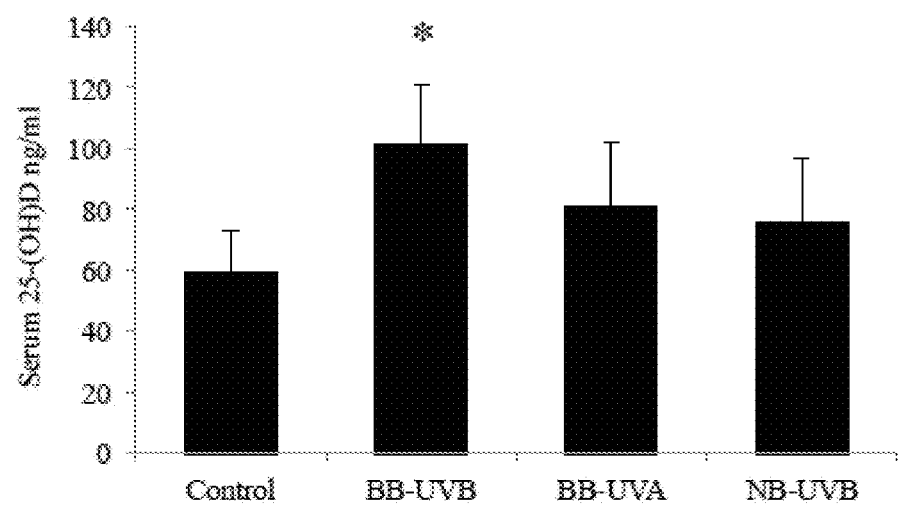

25-Hydroxyvitamin $D_3$ was measured as an indicator of vitamin D production in vivo. There was no significant change 25(OH)D3 after BB-UVB, UVA-1 and NB-UVB radiation for 37 days at ~2.5 KJ/m₂ (FIG. 5A). A statistically significant increase in serum 25(OH)D3 was achieved only by the 10.0 KJ/m2 per day of BB-UVB (FIG. 5B).

TABLE 3

Suppression of EAE by BB-UVB and BB-UVA

| Treatment | Incidence | Day of onset | Mean Severity | CDI |
|---|---|---|---|---|
| Control | 100% (12/12) | 12 ± 2 | 2.6 ± 0.3 | 51 ± 7 |
| BB-UVB 2.5 KJ/m² | 92% (11/12) | 16 ± 3* | 1.7 ± 0.8* | 25 ± 16* |
| BB-UVB 10.0 KJ/m² | 97% (8/12) | 20 ± 4* | 1.4 ± 0.6* | 10 ± 9* |
| BB-UVA 2.5 KJ/m² | 100% (12/12) | 15 ± 3* | 2.3 ± 0.5# | 38 ± 13* |
| BB-UVA 10.0 KJ/m² | 75% (9/12) | 14 ± 1* | 1.7 ± 0.9*# | 23 ± 17*# |

*vs Control;
vs BB-UVB

Discussion

It is well accepted that the incidence of MS is lowest at the equator and increases dramatically with distance from the equator [27]. This led Goldberg to suggest that MS incidence is inversely related to sunlight exposure [28]. Not surprising, a decreased production of vitamin D correlated with an increased incidence of MS [29]. Administration of the hormonal form of vitamin D, i.e. 1,25-(OH)$_2$D$_3$ clearly suppresses the symptoms of EAE, a model of MS in mice [30, 31]. However, this is associated with hypercalcemia when diets adequate in calcium are fed [13]. Furthermore, 1,25-(OH)$_2$D$_3$ has little effect on EAE when diets devoid of calcium are fed [13].

Hypercalcemia produced by doses of exogenous parathyroid hormone itself, independent of vitamin D, suppresses EAE in female mice [32]. Of great importance are the two independent reports that vitamin D deficiency does not increase the incidence or severity of EAE but unexpectedly suppresses EAE [10, 11], a finding confirmed by yet another report [12]. This is also supported by the finding that VDR KO mice fail to develop EAE [12]. These results cast serious doubt that vitamin D production mediates the suppressive effect of UV light on EAE and probably MS. The result of Becklund et al. [7] demonstrates that UV light suppresses EAE symptoms independent of vitamin D. The present results show that UV-A and C do not provide a suppressive effect on EAE and the wavelength between 280 and 340 nm is effective. This effectiveness is largely captured by a narrow band of UV light between 300 and 315 nm with a peak at 311 nm. This wave length does not increase serum 25(OH)D3 adding fuel to the idea that the relationship between UV light and suppression of MS is not through vitamin D production [7]. An additional advantage of the NB light is that it is much less damaging than the BB UV light. We suggest that this NB UV light may be very effective on human MS and should be tested.

NB light is currently used to treat plaque psoriasis [33]. It is safe and has efficacy [34]. This possibility is encouraging because the NB lacks the damaging wavelengths attributed to BB UV.

An important question is how this narrow band UV light can suppress EAE. Release of cytokines from epidermis might well be a mechanism although evidence for such a mechanism is not yet available. It is equally possible that an unknown compound found in skin might be converted to an agent following absorption of the NB UV light.

REFERENCES

1. Holmoy T (2008) The immunology of multiple sclerosis: disease mechanisms and therapeutic targets. *Minerva Med* 99(2):119-140.
2. Ebers G C & Sadovnick A D (1993) The geographic distribution of multiple sclerosis: a review. *Neuroepidemiology* 12(1):1-5.
3. Jones G, Strugnell S A, & DeLuca H F (1998) Current understanding of the molecular actions of vitamin D. *Physiol Rev* 78(4):1193-1231.
4. Woolmore J A, et al. (2007) Studies of associations between disability in multiple sclerosis, skin type, gender and ultraviolet radiation. *Mult Scler* 13(3):369-375.
5. Cantorna M T (2012) Vitamin D, multiple sclerosis and inflammatory bowel disease. *Arch Biochem Biophys* 523 (1):103-106.
6. Garcion E, et al. (2003) Treatment of experimental autoimmune encephalomyelitis in Rat by 1,25-dihydroxyvitamin D$_3$ leads to early effects within the central nervous system. *Acta Neuropathol* 105(5):438-448.
7. Becklund B R, Severson K S, Vang S V, & DeLuca H F (2010) UV radiation suppresses experimental autoimmune encephalomyelitis independent of vitamin D production. *Proc Natl Acad Sci USA* 107(14):6418-6423.
8. Hart P H, Gorman S, & Finlay-Jones J J (2011) Modulation of the immune system by UV radiation: more than just the effects of vitamin D? *Nat Rev Immunol* 11(9): 584-596.
9. Juzeniene A & Moan J (2012) Beneficial effects of UV radiation other than via vitamin D roduction. *Dermatoendocrinol* 4(2):109-117.
10. DeLuca H F & Plum L A (2011) Vitamin D deficiency diminishes the severity and delays onset of experimental autoimmune encephalomyelitis. *Arch Biochem Biophys* 513(2):140-143.
11. Fernandes de Abreu D A, Ibrahim E C, Boucraut J, Khrestchatisky M, & Feron F (2010) Severity of experimental autoimmune encephalomyelitis is unexpectedly reduced in mice born to vitamin D-deficient mothers. *J Steroid Biochem Mol Biol* 121(1-2):250-253.
12. Wang Y, Marling S J, Zhu J G, Severson K S, & DeLuca H F (2012) Development of experimental autoimmune encephalomyelitis (EAE) in mice requires vitamin D and the vitamin D receptor. *Proc Natl Acad Sci USA* 109(22): 8501-8504.
13. Cantorna M T, Humpal, Winter J, & DeLuca H F (1999) Dietary calcium is a major factor in 1,25-dihydroxycholecalciferol suppression of experimental autoimmune encephalomyelitis in mice. *J Nutr* 129(11):1966-1971.

14. Matsumura Y & Ananthaswamy H N (2004) Toxic effects of ultraviolet radiation on the skin. *Toxicol Appl Pharmacol* 195(3):298-308.
15. Menage H D, Harrison G I, Potten C S, Young A R, & Hawk J L (1995) The action spectrum for induction of chronic actinic dermatitis is similar to that for sunburn inflammation. *Photochem Photobiol* 62(6):976-979.
16. Kripke M L (1974) Antigenicity of murine skin tumors induced by ultraviolet light. *J Natl Cancer Inst* 53(5): 1333-1336.
17. Norval M, McLoone P, Lesiak A, & Narbutt J (2008) The effect of chronic ultraviolet radiation on the human immune system. *Photochem Photobiol* 84(1):19-28.
18. Sreevidya C S, et al. (2010) Agents that reverse UV-Induced immune suppression and photocarcinogenesis affect DNA repair. *J Invest Dermatol* 130(5):1428-1437.
19. Venditti E, Bruge F, Astolfi P, Kochevar I, & Damiani E (2011) Nitroxides and a nitroxide-based UV filter have the potential to photoprotect UVA-irradiated human skin fibroblasts against oxidative damage. *J Dermatol Sci* 63(1):55-61.
20. De Fabo E C, Noonan F P, Fears T, & Merlino G (2004) Ultraviolet B but not ultraviolet A radiation initiates melanoma. *Cancer Res* 64(18):6372-6376.
21. Zandi S, Kalia S, & Lui H (2012) UVA1 phototherapy: a concise and practical review. *Skin Therapy Lett* 17(1):1-4.
22. Grabbe J, et al. (1996) High-dose ultraviolet A1 (UVA1), but not UVA/UVB therapy, decreases IgE-binding cells in lesional skin of patients with atopic eczema. *J Invest Dermatol* 107(3):419-422.
23. Bulat V, Situm M, Dediol I, Ljubicic I, & Bradic L (2011) The mechanisms of action of phototherapy in the treatment of the most common dermatoses. *Coll Antropol* 35 Suppl 2:147-151.
24. Schmidt-Gayk H, Bouillon R, & Roth H J (1997) Measurement of vitamin D and its metabolites (calcidiol and calcitriol) and their clinical significance. *Scand J Clin Lab Invest Suppl* 227:35-45.
25. Hauser S L, et al. (1984) Prevention of experimental allergic encephalomyelitis (EAE) in the SJL/J mouse by whole body ultraviolet irradiation. *J Immunol* 132(3):1276-1281.
26. Cavaletti G, et al. (2004) Extracorporeal photochemotherapy reduces the severity of Lewis rat experimental allergic encephalomyelitis through a modulation of the function of peripheral blood mononuclear cells. *J Biol Regul Homeost Agents* 18(1):9-17.
27. Simpson S, Jr., Blizzard L, Otahal P, Van der Mei I, & Taylor B (2011) Latitudeis significantly associated with the prevalence of multiple sclerosis: a meta-analysis. *J Neurol Neurosurg Psychiatry* 82(10):1132-1141.
28. Agranoff B W & Goldberg D (1974) Diet and the geographical distribution of multiple sclerosis. *Lancet* 2(7888):1061-1066.
29. Runia T F, Hop W C, de Rijke Y B, Buljevac D, & Hintzen R Q (2012) Lower serum vitamin D levels are associated with a higher relapse risk in multiple sclerosis. *Neurology* 79(3):261-266.
30. Lemire J M & Archer D C (1991) 1,25-dihydroxyvitamin $D_3$ prevents the in vivo induction of murine experimental autoimmune encephalomyelitis. *J Clin Invest* 87(3):1103-1107.
31. Cantorna M T, Hayes C E, & DeLuca H F (1996) 1,25-Dihydroxyvitamin $D_3$ reversibly blocks the progression of relapsing encephalomyelitis, a model of multiple sclerosis. *Proc Natl Acad Sci USA* 93(15):7861-7864.
32. Meehan T F, Vanhooke J, Prahl J, & Deluca H F (2005) Hypercalcemia produced by parathyroid hormone suppresses experimental autoimmune encephalomyelitis in female but not male mice. *Arch Biochem Biophys* 442(2):214-221.
33. Nishida E, et al. (2011) Successful treatment of psoriasis vulgaris with targeted narrow-band ultraviolet B therapy using a new flat-type fluorescent lamp. *Photodermatol Photoimmunol Photomed* 27(5):248-250.
34. Weischer M, Blum A, Eberhard F, Rocken M, & Berneburg M (2004) No evidence for increased skin cancer risk in psoriasis patients treated with broadband or narrowband UVB phototherapy: a first retrospective study. (Translated from eng) *Acta Derm Venereol* 84(5):370-374 (in eng).
35. Tremlett H et al., (2008) Monthly ambient sunlight, infections and relapse rates in multiple sclerosis. *Neuroepidemiology* 31(4):271-279).
36. Compston A, Coles A, October 2008, Multiple sclerosis. Lancet 372 (9648): 1502-17.
37. Trojano M, Paoliceili D, (2001) The differential diagnosis of multiple sclerosis: classification and clinical features of relapsing and progressive neurological syndromes. *Neurol, Sci.* 22 (Suppl 2): S98-102.
38. Poser C M, Brinar V V (2004) Diagnostic criteria for multiple sclerosis: an historical review. *Clin Neurol Neurosurg* 108 (3): 147-58.
39. McDonald W I, Compston A, Edan G et al, (2001) Recommended diagnostic criteria for multiple sclerosis: guidelines from the International Panel on the diagnosis of multiple sclerosis. *Ann. Neurol.* 50 (1): 121-7.
40. Polman C H, Reingold S C, Edan G et al., (2005) Diagnostic criteria for multiple sclerosis: 2005 revisions to the "McDonald Criteria". *Ann. Neurol,* 58 (6): 840-6.
41. Gronseth G S, Ashman E J, (2000) Practice parameter: the usefulness of evoked potentials in identifying clinically silent lesions in patients with suspected multiple sclerosis (an evidence-based review): Report of the Quality Standards Subcommittee of the American Academy of Neurology. *Neurology* 54 (9): 1720-5
42. Link H, Huang Y M, (2008) Oligoclonai bands in multiple sclerosis cerebrospinal fluid: an update on methodology and clinical usefulness. *J. Neuroimmunol.* 180 (1-2): 17-28.

We claim:
1. A method for suppressing clinical symptoms of multiple sclerosis (MS) in a subject showing the clinical symptoms of MS, the method comprising:
   (a) treating the subject, the treatment consisting of: irradiating the whole body of the subject with one or more effective doses of light produced from a device including a light emitter, the subject showing clinical symptoms of MS, wherein the one or more doses of light are effective to suppress the clinical symptoms of MS;
      wherein the one or more doses of light do not alter the vitamin D level in the subject;
      wherein the one or more doses of light comprise an energy density of at least 2.5 $kJ/m^2$; and
      wherein the one or more doses of light are characterized by a wavelength within a range from 290 nm to 320 nm;
   (b) detecting a suppression of the clinical symptoms of MS in the subject, wherein the detecting includes detecting of one or more of a delay of onset of the clinical symptoms of MS, a reduction of peak of severity of the clinical symptoms of MS, and a decrease of cumulative disease index (CDI).

2. The method of claim 1 wherein the one or more doses of light have a wavelength between 300 nm and 315 nm.

3. The method of claim 1 wherein the majority of light from the device including the light emitter is within 300 nm-315 nm.

4. The method of claim 1 where at least 95% of the light from the device including the light emitter is within 300 nm-315 nm.

5. The method of claim 1, where the irradiation of step (a) is irradiating the whole body of the subject with an effective first dose of light from the device including the light emitter, wherein the majority of light emitted is in the range of 300-315 nm.

6. The method of claim 5, wherein the irradiation of step (a) is irradiating the whole body of the subject with the effective first dose of light from the device including the light emitter, wherein at least 90% of the light emitted is in the range of 300-315 nm.

7. The method of claim 5, wherein the irradiation of step (a) is irradiating the whole body of the subject with the effective first dose of light from the device, wherein the device comprises a blanket or fabric covering.

8. The method of claim 5, wherein the irradiation of step (a) is irradiating the whole body of the subject with the effective first dose of light from the device including the light emitter is contained within a housing.

9. The method of claim 1, wherein in step (a), the whole body of the subject is irradiated with a first effective dose of light and a second effective dose of light.

10. The method of claim 9, wherein the first effective dose of light and the second effective dose of light are the same.

11. The method of claim 9, wherein the first effective dose of light and the second effective dose of light are different.

12. The method of claim 9, wherein the second effective dose is a repeated dose.

13. The method of claim 9, wherein the one or more doses of light do not increase the vitamin D level in the subject by more than 5 ng/ml.

* * * * *